United States Patent
Ramanan et al.

(10) Patent No.: US 9,682,208 B2
(45) Date of Patent: Jun. 20, 2017

(54) METHODS AND APPARATUS FOR ADAPTABLE PRESSURE TREATMENT OF SLEEP DISORDERED BREATHING

(75) Inventors: Dinesh Ramanan, Bella Vista (AU); Jeffrey Peter Armitstead, Bella Vista (AU); Dion Charles Chewe Martin, Bella Vista (AU)

(73) Assignee: ResMed Limited (AU)

(*) Notice: Subject to any disclaimer, the term of this patent is extended or adjusted under 35 U.S.C. 154(b) by 797 days.

(21) Appl. No.: 13/509,880

(22) PCT Filed: Nov. 16, 2010

(86) PCT No.: PCT/AU2010/001536
§ 371 (c)(1),
(2), (4) Date: May 15, 2012

(87) PCT Pub. No.: WO2011/057362
PCT Pub. Date: May 19, 2011

(65) Prior Publication Data
US 2012/0291785 A1    Nov. 22, 2012

Related U.S. Application Data

(60) Provisional application No. 61/261,562, filed on Nov. 16, 2009.

(51) Int. Cl.
*A61M 16/00* (2006.01)

(52) U.S. Cl.
CPC .... *A61M 16/0051* (2013.01); *A61M 16/0069* (2014.02); *A61M 2016/0027* (2013.01);
(Continued)

(58) Field of Classification Search
CPC .......... A61M 16/0069; A61M 16/0066; A61M 15/00; A61M 2016/0039;
(Continued)

(56) References Cited

U.S. PATENT DOCUMENTS 5,199,424 A    4/1993  Sullivan et al.
5,245,995 A *  9/1993  Sullivan et al. ......... 128/204.23
(Continued)

FOREIGN PATENT DOCUMENTS

JP    2004-526470 A    9/2004
JP      2005161068 A    6/2005
(Continued)

OTHER PUBLICATIONS

International Search Report Application No. PCT/AU2010/001536, dated Mar. 25, 2011.
(Continued)

*Primary Examiner* — Lynne Anderson
*Assistant Examiner* — Elliot S Ruddie
(74) *Attorney, Agent, or Firm* — Lerner, David, Littenberg, Krumholz & Mentlik, LLP

(57) ABSTRACT

Respiratory pressure treatment apparatus include automated methodologies for controlling changes to pressure in the presence of sleep disordered breathing events. In an example apparatus, various levels of expiratory pressure relief can provide different pressure reductions for patient comfort during expiration (333-A, 333-B, 333-C). The control parameters for these levels may be automatically modified based on the detection of an open airway. Similarly, in some embodiments, the levels may be automatically adjusted based on a detection of persistent obstruction. In still further embodiments, control parameters associated with a rise time of an early portion of an inspiratory pressure treatment may be automatically adjusted upon detection of flow limitation to permit a change to more aggressive waveforms from more comfortable waveforms for the treatment of sleep disordered breathing events.

24 Claims, 10 Drawing Sheets

(52) U.S. Cl.
CPC ............... *A61M 2016/0039* (2013.01); *A61M 2205/502* (2013.01)

(58) Field of Classification Search
CPC ...... A61M 2016/0042; A61M 16/0051; A61M 16/00; A61M 16/0003; A61M 16/0045; A61M 16/0057; A61M 16/06; A61M 16/0616; A61M 16/0633; A61M 16/0644; A61M 16/0666; A61M 16/0683; A61M 16/0694; A61M 16/08; A61M 16/0833; A61B 2562/0219; A61B 5/00; A61B 5/0031; A61B 5/0205; A61B 5/02055; A61B 5/0215; A61B 5/02405; A61B 5/036; A61B 5/0421; A61B 5/0422; A61B 5/0464; A61B 5/0476; A61B 5/0488; A61B 5/0496; A61B 5/053; A61B 5/0538
USPC ............ 128/204.18, 204.21, 204.22, 204.23, 128/204.26, 200.24, 201.26, 201.28, 128/202.22, 205.11, 205.24, 205.25, 128/206.12, 206.18, 206.21, 206.23, 128/206.24, 206.27, 207.11, 207.12, 128/207.13, 207.15, 207.17, 207.18, 848; 600/529, 530–543
See application file for complete search history.

(56) References Cited

U.S. PATENT DOCUMENTS

| | | |
|---|---|---|
| 5,490,502 A | 2/1996 | Rapoport et al. |
| 5,492,113 A | 2/1996 | Estes et al. |
| 5,535,738 A * | 7/1996 | Estes ..................... A61M 16/00 128/204.21 |
| 5,549,106 A | 8/1996 | Gruenke et al. |
| 5,645,053 A | 7/1997 | Remmers et al. |
| 5,704,345 A | 1/1998 | Berthon-Jones |
| 5,803,066 A | 9/1998 | Rapoport et al. |
| 6,532,960 B1 * | 3/2003 | Yurko ..................... 128/204.26 |
| 6,640,806 B2 | 11/2003 | Yurko |
| 7,128,069 B2 | 10/2006 | Farrugia et al. |
| 2002/0088465 A1 | 7/2002 | Hill |
| 2003/0121519 A1 | 7/2003 | Estes et al. |
| 2007/0142741 A1 | 6/2007 | Berthon-Jones et al. |
| 2008/0000478 A1 * | 1/2008 | Matthiessen et al. ... 128/204.23 |
| 2008/0066753 A1 | 3/2008 | Martin et al. |
| 2008/0202528 A1 * | 8/2008 | Carter et al. ............. 128/204.23 |
| 2009/0205662 A1 | 8/2009 | Kwok et al. |

FOREIGN PATENT DOCUMENTS

| | | |
|---|---|---|
| JP | 2008110221 A | 5/2008 |
| WO | 99/61088 A1 | 12/1999 |
| WO | 02/26283 A2 | 4/2002 |
| WO | 2004112680 A2 | 12/2004 |
| WO | 2006034549 A2 | 4/2006 |
| WO | 2007140512 A1 | 12/2007 |
| WO | 2008/138040 A1 | 11/2008 |
| WO | 2011006199 A1 | 1/2011 |

OTHER PUBLICATIONS

European Search Report for Application No. EP10829379 dated Apr. 30, 2015.

* cited by examiner

| Obstruction Index | T1 | T2 | T3 | ... | TN |
|---|---|---|---|---|---|
| 0 | 1% | 2% | 3% | ... | 100% |
| 1 | 1% | 4% | 6% | ... | 100% |
| 2 | 1% | 8% | 10% | ... | 100% |
| ... | ... | ... | ... | ... | ... |
| N | 1% | 20% | 30% | ... | 100% |

Fig. 8

METHODS AND APPARATUS FOR ADAPTABLE PRESSURE TREATMENT OF SLEEP DISORDERED BREATHING

CROSS REFERENCE TO RELATED APPLICATONS

The present application is a national phase entry under 35 U.S.C. §371 of International Application No. PCT/AU2010/001536 filed Nov. 16, 2010, published in English, which claims priority from U.S. Provisional Application No. 61/261,562 filed Nov. 16, 2009 all of which are incorporated herein by reference.

FIELD OF THE TECHNOLOGY

The present technology relates to methods and apparatus for controlling treatment of sleep disordered breathing. More particularly, it relates to methods and apparatus for pressure control in the treatment of sleep disordered breathing.

BACKGROUND OF THE TECHNOLOGY

As described by Sullivan & Lynch in U.S. Pat. No. 5,199,424, issued on Apr. 6, 1993, the application of continuous positive airway pressure (CPAP) has been used as a means of treating the occurrence of obstructive sleep apnea. The patient is connected to a positive pressure air supply by means of a nose mask or nasal prongs. The air supply breathed by the patient is slightly greater than atmospheric pressure. It has been found that the application of continuous positive airway pressure provides what can be described as a "pneumatic splint", supporting and stabilizing the upper airway and thus eliminating the occurrence of upper airway occlusions. It is effective in eliminating both snoring and, obstructive sleep apnea and in many cases, is effective in treating central and mixed apnea.

In U.S. Pat. No. 5,549,106 to Gruenke, issued on Aug. 27, 1996, an apparatus is disclosed that is intended for facilitating the respiration of a patient for treating mixed and obstructive sleep apnea. The device is said to increase nasal air pressure delivered to the patient's respiratory passages just prior to inhalation and by subsequently decreasing the pressure is said to ease exhalation effort.

In U.S. Pat. No. 5,245,995 Sullivan discusses how snoring and abnormal breathing patterns can be detected by inspiration and expiration pressure measurements while sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to, ideally, subvert the occurrence of the obstructive episodes and the other forms of breathing disorder.

As described by Berthon-Jones in U.S. Pat. No. 5,704,345, issued on Jan. 6, 1998, various techniques are known for sensing and detecting abnormal breathing patterns indicative of obstructed breathing, the disclosures of which are incorporated herein by reference. Berthon-Jones describes methods based on detecting events such as apnea, snoring, and respiratory flow limitation, e.g. flattening of the inspiratory portion of a flow curve. Treatment pressure may be automatically adjusted in response to the detected conditions. Berthon-Jones also describes methods for detecting central apneas.

Other methods for detecting obstruction have also been used. For example, in. U.S. Pat. Nos. 5,490,502 and 5,803,066, Rapoport is said to disclose a method and apparatus for optimizing the controlled positive pressure to minimize the flow of air from a flow generator while attempting to ensure that flow limitation in the patient's airway does not occur. Controlled positive pressure to the airway of a patient is said to be adjusted by detecting flow limitation from the shape of an inspiratory flow waveform. The CPAP pressure setting is raised, lowered or maintained depending on whether flow limitation has been detected and on the previous actions taken by the system.

In U.S. Pat. No. 5,645,053, Remmers is said to describe a system for automatically and continuously regulating the level of nasal pressure to an optimal value during OSA (Obstructive Sleep Apnea) treatment. Parameters related to the shape of a time profile of inspiratory flow are determined including a degree of roundness and flatness of the inspiratory profile. OSA therapy is then implemented by automatically re-evaluating an applied pressure and continually searching for a minimum pressure required to adequately distend a patient's pharyngeal airway.

Another type of device for treating sleep disordered breathing is the device disclosed by Farrugia and Alder in International Patent Application No. PCT/US2004019598 (Publ. No. WO 2004/112680) and corresponding U.S. Pat. No. 7,128,069, the disclosure of which is incorporated herein by reference. A CPAP pressure that is delivered to the patient may be adjusted to treat sleep disordered breathing events such as detected partial or complete obstruction. The delivered pressure may be slightly reduced from the set CPAP pressure upon detection of patient expiration. This expiratory pressure relief (EPR) can provide comfort for the patient while the patient exhales since it may be easier to exhale at the reduced pressure when compared to the higher CPAP pressure. The delivered pressure is then returned to the set CPAP pressure upon detection of patient inspiration.

Despite the availability of such devices for treating OSA, some sleep disordered breathing events may still go untreated with the use of some devices. Thus, it will be appreciated that there may be a need for improved techniques and devices for addressing the conditions of sleep disordered breathing while balancing the desire for patient comfort.

BRIEF SUMMARY OF THE TECHNOLOGY

An aspect of certain example embodiments of the present technology relates to automated control methodologies for respiratory pressure treatment apparatus implemented to treat sleep disordered breathing.

Another aspect of some embodiments the present technology is the automated control of adjustments to pressure settings or pressure control parameters upon a detection of sleep disordered breathing events.

In some embodiments, automated control of various levels or magnitudes of expiratory pressure relief can provide different pressure reductions for patient comfort during expiration. In some embodiments, the control parameters for these levels may be automatically modified based on the detection of an open airway, such as a detection of an open airway that may be contemporaneous with a detection of an apnea and/or a reduction in a measure of patient airflow or patient ventilation. Similarly, in, some embodiments, the levels may be automatically adjusted based on a detection of persistent obstruction. In still further embodiments, control parameters associated with a rise time of an early portion of an inspiratory pressure treatment may be automatically adjusted upon detection of flow limitation. This can change the delivered pressure to more aggressive waveforms from more comfortable waveforms for the treatment of sleep disordered breathing.

In accordance with one aspect of the present technology, an adaptive form of positive airway pressure treatment is provided, for example, in treatment of sleep disordered breathing. Preferably, the shape of a pressure-time curve is modified based on detection of respiratory conditions. More preferably, in response to detection of flow limitation, or partial obstruction of the airway, a pressure-time curve may be more aggressive, or with a larger or steeper gradient compared to those occasions when flow limitation, or partial obstruction is not detected, when the shape of the pressure time curve may be more gentle, or with a smaller, or more shallow gradient. More preferably, an initial rise of pressure is modified based on detection of respiratory conditions. More preferably, a pressure-time curve during an expiratory portion of a breathing cycle of the patient is modified. In an additional or alternative form, a magnitude of a change in pressure during an expiratory portion of a breathing cycle of a patient is modified based on detection of respiratory conditions. In one form, upon detection of a first group of respiratory events, a magnitude of change of pressure during exhalation is increased, upon detection of a second group of respiratory events, a magnitude of change of pressure during exhalation is decreased, and upon detection of a third group of respiratory events, the magnitude of change of pressure during exhalation is left unchanged. Preferably, the first group includes the absence of detection of flow limitation. Preferably the second group includes detection of the presence of flow limitation, or the continued presence of flow limitation. In one form, upon the detection of persistent obstruction a CPAP pressure may be increased, while leaving a magnitude of change of pressure during an expiratory portion of the breathing cycle unchanged.

In an example embodiment, a respiratory pressure treatment apparatus includes a flow generator to generate a flow of breathable gas to a patient interface. Optionally, the apparatus may include a sensor to measure the flow of breathable gas. A controller of the apparatus is configured to control the flow generator to deliver a flow of breathable gas with inspiratory pressure portions and expiratory pressure portions that are synchronized with expiration and inspiration. In this delivered flow, an expiratory pressure portion may be at a pressure lower than an inspiratory pressure portion. The controller may also be configured to control a detection of an open airway apnea (e.g., by detecting an absence of a breath or a flow limited breath) from the measure of flow and to modify control parameters of an expiratory pressure portion based on the detection of the open airway to decrease a reduction in expiratory pressure while still permitting a reduction in expiratory pressure for the expiratory pressure portion.

Additionally or alternatively, the presence of absence of flow limitation and/or open airway is detected using a pressure sensor. Additionally or alternatively, an effort sensor is used to detect and or distinguish a respiratory condition of a person. Additionally or alternatively, a movement sensor is used to detect and or distinguish a respiratory condition of the person.

In some embodiments of the apparatus, the detection of open airway comprises a detection of central apnea and/or a detection of central hypopnea. Optionally, the controller may be further configured to discontinue the modification of the expiratory pressure portion in response to a detection of an absence of central apneas over a period of time.

In still further embodiments, the respiratory pressure treatment apparatus may have a controller to control the flow generator to deliver a synchronized flow of breathable gas with expiratory pressure portion or portions and inspiratory pressure portion or portions such that at least one of the expiratory pressure portions is at a pressure lower than at least one of the inspiratory pressure portions. The controller may also be configured to control a detection of persistent obstruction to flow from a measure of flow and to modify control parameters of an expiratory pressure portion to change a pressure delivered during the expiratory pressure portion based on the detection of the persistent obstruction.

In some such embodiments, the controller is configured to modify the expiratory pressure portion as a decrease in a reduction of expiratory pressure for an expiratory phase. Optionally, the controller may also be configured to modify the expiratory pressure portion subsequent to one or more automated increases in a pressure of the expiratory pressure portion made in response to a detection of flow limitation. Optionally, the controller may be configured to detect flow limitation by a detection of partial obstruction or obstructive apnea. In some embodiments, controlled modifications of the expiratory pressure portion may include disabling expiratory pressure relief during an expiratory phase. In still other embodiments, the controller may be configured to discontinue the modification of the expiratory pressure portion in response to a detection of an absence of obstruction over a period of time.

In some embodiments of the respiratory pressure treatment apparatus, the controller may be configured to control the flow generator to deliver a synchronized flow of breathable gas at a patient interface with an inspiratory pressure portion and an expiratory pressure portion such that the inspiratory pressure portion peaks at a first pressure higher than the expiratory pressure. The controller may then be further configured to control a detection of flow limitation from the measure of flow and to modify a pressure rise time of an early part of the inspiratory pressure portion based on the detection of flow limitation. The controller may then control a generation of a further flow of breathable gas at the patient interface having an inspiratory pressure portion that peaks at the first pressure and rises in accordance with the modified pressure rise time. For example, in some versions, the modified pressure rise time is decreased so as to form a more aggressive inspiratory pressure portion with the further flow than the inspiratory pressure portion of the prior flow when the detection of flow limitation represents a presence of obstruction.

In some such embodiments, the controlled modification increases the pressure rise time so as to form a more gentle inspiratory pressure portion with the further flow than the inspiratory pressure portion of the prior flow when the detection of flow limitation represents an absence of obstruction.

In some embodiments, the modification of the pressure rise time of the early part may be implemented by a selection of a set of values from a look-up table as a function of the determined flow limitation. Optionally, the look-up table may include scaling factors representative of a plurality of inspiratory pressure waveforms with different rise times.

In some embodiments of the technology, a respiratory pressure treatment apparatus includes a flow generator to generate a flow of breathable gas to a patient interface. A controller of the apparatus controls the flow generator to deliver a flow of breathable gas at a patient interface. The flow of breathable gas is synchronized with a respiratory cycle. The flow of breathable gas also comprises expiratory pressure portions and inspiratory pressure portions wherein at least one of the expiratory pressure portions is at a pressure lower than at least one of the inspiratory pressure portions. In the apparatus, the controller may also be configured to control a detection of sleep state. It may be further configured to change a control parameter for a rise time of said inspiratory pressure portions based on a detection of the sleep state.

For example, the controller may adjust the control parameter to decrease a rise time in response to a detection of a sleep state indicative of sleep. Moreover, the controller may ramp the control parameter to gradually decrease a rise time in response to a detection of a sleep state indicative of sleep. Optionally, the controller adjusts the control parameter to increase a rise time in response to a detection of a sleep state indicative of wakefulness. Still further, the controller may ramp the control parameter to gradually increase a rise time in response to a detection of a sleep state indicative of wakefulness. Optionally, in response to a detection of a sleep state indicative of sleep, the controller may initiate a control protocol for adjusting the control parameter for the rise time based on detection of a sleep disordered breathing event. Furthermore, in response to a detection of a sleep state indicative of wakefulness, the controller may disengage a control protocol for adjusting the control parameter for the rise time based on detection of a sleep disordered breathing event.

In still further embodiments of the technology, a respiratory pressure treatment apparatus includes a flow generator to generate a flow of breathable gas to a patient interface. A controller of the apparatus controls the flow generator to deliver a flow of breathable gas at a patient interface. The flow of breathable gas is synchronized with a respiratory cycle. The flow of breathable gas also comprises expiratory pressure portions and inspiratory pressure portions wherein at least one of the expiratory pressure portions is at a pressure lower than at least one of the inspiratory pressure portions. The controller of the apparatus may also control a determination of a measure of ventilation. The controller may then control a change to control parameters of an expiratory pressure portion to modify a reduction in expiratory pressure while still permitting a reduction in expiratory pressure for the expiratory pressure portion, the controlled change being a function of the measure of ventilation. For example, the function of the measure of ventilation may comprises a comparison of the measure and a target ventilation. In some such cases, the reduction is decreased if the target ventilation exceeds the measure of ventilation. In still other cases, the reduction is increased if the measure of ventilation exceeds the target ventilation.

In some embodiments, the controller may be configured to control a change to a control parameter for a rise time of said inspiratory pressure portions where the controlled change may be a function of the measure of ventilation. For example, the function of the measure of ventilation may comprise a comparison of the measure and a target ventilation. In some cases, the rise time is increased if the target ventilation exceeds the measure of ventilation. In some cases, the rise time is decreased if the measure of ventilation exceeds the target ventilation.

In still further embodiments of the technology, a respiratory pressure treatment apparatus includes a flow generator to generate a flow of breathable gas to a patient interface. A controller of the apparatus controls the flow generator to deliver a flow of breathable gas at a patient interface. The flow of breathable gas is synchronized with a respiratory cycle. The flow of breathable gas also comprises expiratory pressure portions and inspiratory pressure portions wherein at least one of the expiratory pressure portions is at a pressure lower than at least one of the inspiratory pressure portions. Optionally, the controller may control an activation of a pre-termination pressure treatment protocol during a pre-termination period wherein a change to control parameters for setting pressure of the inspiratory pressure portions or the expiratory pressure portion is initiated.

For example, in some embodiments of the pre-termination pressure treatment protocol, the change to control parameters for setting pressure of the expiratory pressure portion comprises an increase in a reduction in expiratory pressure. In some embodiments of the pre-termination pressure treatment protocol, the change to control parameters for setting pressure of the inspiratory pressure portion comprises a decrease in a rise time for an early portion of the inspiratory pressure. In still further embodiments of the pre-termination pressure treatment protocol, the change to control parameters for setting pressure comprises a ramping down of a peak inspiratory pressure. This peak inspiratory pressure may be ramped down in a range from a peak inspiratory level in the treatment before the pre-termination period to a pressure level of an expiratory pressure portion also from the treatment before the pre-termination period. In such a case, the ramping down may comprise a gradual reduction of the peak inspiratory pressure extending over the pre-termination period. In some such embodiments, the controller may initiate the pre-termination period as a function of a pre-set termination time. Optionally, the controller may initiate the pre-termination period as a function a detection by the controller of a lapsed time in a sleep state attributable to sleep. Still further, the controller may initiate the pre-termination period as a function of a detection by the controller of a sleep state attributable to wakefulness.

Various aspects of the described example embodiments may be combined with aspects of certain other example embodiments to realize yet further embodiments.

Other features of the technology will be apparent from consideration of the information contained in the following detailed description.

BRIEF DESCRIPTION OF THE DRAWINGS

The present technology is illustrated by way of example, and not by way of limitation, in the figures of the accompanying drawings, in which like reference numerals refer to similar elements including:

FIG. 8 is a data table with illustrative inspiratory pressure waveform scaling factor data in accordance with an example embodiment of the methodology of FIG. 6;

DETAILED DESCRIPTION

Figure 1:
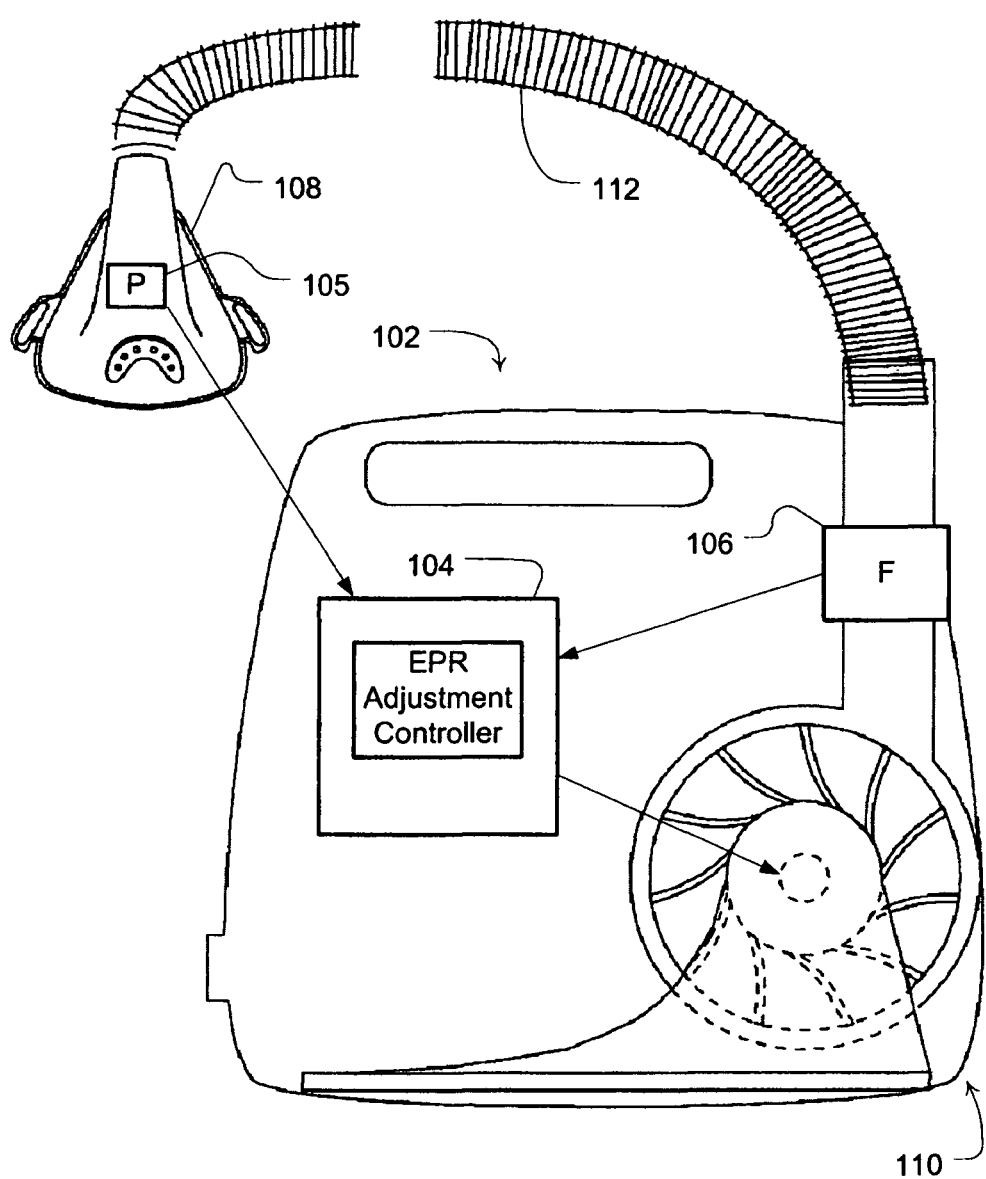
FIG. 1 illustrates example components of a respiratory pressure treatment device of the present technology.

The present technology involves methods and devices for the treatment of patients with sleep disordered breathing (SDB). One embodiment of a respiratory pressure treatment apparatus 102 for implementing the present technology is illustrated in FIG. 1. In the embodiment, the device includes a controller 104 to detect SDB events and make changes to treatment pressure in accordance with one or more control methodologies. The apparatus 102 will also include a flow generator such as such a servo-controlled blower 110. The apparatus may be configured for coupling with a patient interface, such as a delivery tube 112 and a mask 108. The mask may optionally be a nasal mask, nose & mouth mask, full-face mask or nasal pillows or other device to provide a seal with the patient's respiratory system so as to permit a pressure treatment at one or more pressures above atmospheric or ambient pressure.

The apparatus 102 also may include sensors, such as a pressure sensor 105 and/or flow sensor 106. In such an embodiment, the pressure sensor 105, such as a pressure transducer, may measure the pressure generated by the blower 110 and generate a pressure signal p(t) indicative of the measurements of pressure. Similarly, the flow, sensor generates a signal representative of the patient's respiratory flow. For example, flow proximate to the patient interface 108 or a sense tube (not shown) may be measured using a pneumotachograph and differential pressure transducer or similar device such as one employing a bundle of tubes or ducts to derive a flow signal f(t). Other sensors may be utilized to generate data indicative of flow or pressure for the purposes of the control methodologies of the apparatus.

Based on flow f(t) and pressure p(t) signals, the controller 104 with one or more processors generates blower control signals. For example, the controller may generate a desired pressure set point and servo-control the blower to meet the set point by comparing the setpoint with the measured condition of the pressure sensor. Thus, the controller 104 may make controlled changes to the pressure delivered to the patient interface by the blower 110. Optionally, such changes to pressure may be implemented by controlling an exhaust with a mechanical release valve (not shown) to increase or decrease the exhaust while maintaining a relatively constant blower speed. Such changes in pressure may be determined by automated detection of SDB events in the controller by analysis of data from a flow signal as discussed in more detail herein. With such a controller or processor, the apparatus can be used for many different pressure treatment therapies, such as the pressure treatments for sleep, disordered breathing by adjusting a suitable pressure delivery equation.

Thus, the controller 104 will typically include a processor configured to implement particular control methodologies such as the algorithms described in more detail herein. To this end, the controller may include integrated chips, a memory and/or, other control instruction, data or information storage medium. For example, programmed instructions encompassing such a control methodology may be coded on integrated chips in the memory of the device. Such instructions may also or alternatively be loaded as software or firmware using an appropriate data storage medium.

For example, the controller may be configured to generate a CPAP pressure treatment with expiratory pressure relief as described by U.S. Pat. No. 7,128,069, the entire disclosure of which is incorporated herein by reference. Thus, it may set a treatment CPAP pressure for each inspiration, which may be chosen (automatically or manually to treat sleep disordered breathing events) and may reduce the pressure by a chosen level of reduction for expiratory pressure relief (EPR) depending on the control methodologies discussed herein. The EPR levels can make breathing more comfortable for the patient. For example, such an EPR control scheme may be implemented with several different levels or magnitudes of pressure reduction (e.g., Level 0=0 $cmH_2O$; Level 1=1.5 $cmH_2O$, Level 2=2 $cmH_2O$, Level 3.5=3 $cmH_2O$). Additional EPR levels may also be implemented and other pressure amounts may be associated with each level. Thus, if a CPAP pressure is prescribed or automatically adjusted to 8 $cmH_2O$ to treat SDB and a level 2 EPR is chosen, pressure during inspiration would be at the CPAP pressure and pressure during expiration mould be reduced to 6 $cmH_2O$. Known methods for detecting patient inspiratory phase (i.e., triggering) and expiratory phase (i.e., cycling) based on data from the sensors may be implemented for the pressure changes to be synchronized with the respiratory cycle. When the presently set EPR level is changed to another level associated with a lower pressure, it would result in a reduction in Pressure Support ("PS") where pressure support is considered the difference between the inspiratory pressure level ("IPL") and the expiratory pressure level ("EPL"). (i.e., PS=IPL−EPL)).

A. Open Airway EPR Adjustments

In some patients the level of EPR may be enough to amplify an existing predisposition to periodic breathing. The dual level waveform, although comfortable and an inefficient form of ventilation, could drive the arterial $CO_2$ down below the apnoeic threshold and cause a central apnoea. Subsequently, the patient would begin breathing (when the $CO_2$ eupnic threshold is reached). This may constitute a periodic breathing sequence similar to Cheyne-Stokes respiration. Accordingly, in some embodiments of the present technology, the selection of the level of EPR may be automated based on the detection of one or more SDB events to minimize such a situation.

Figure 2:
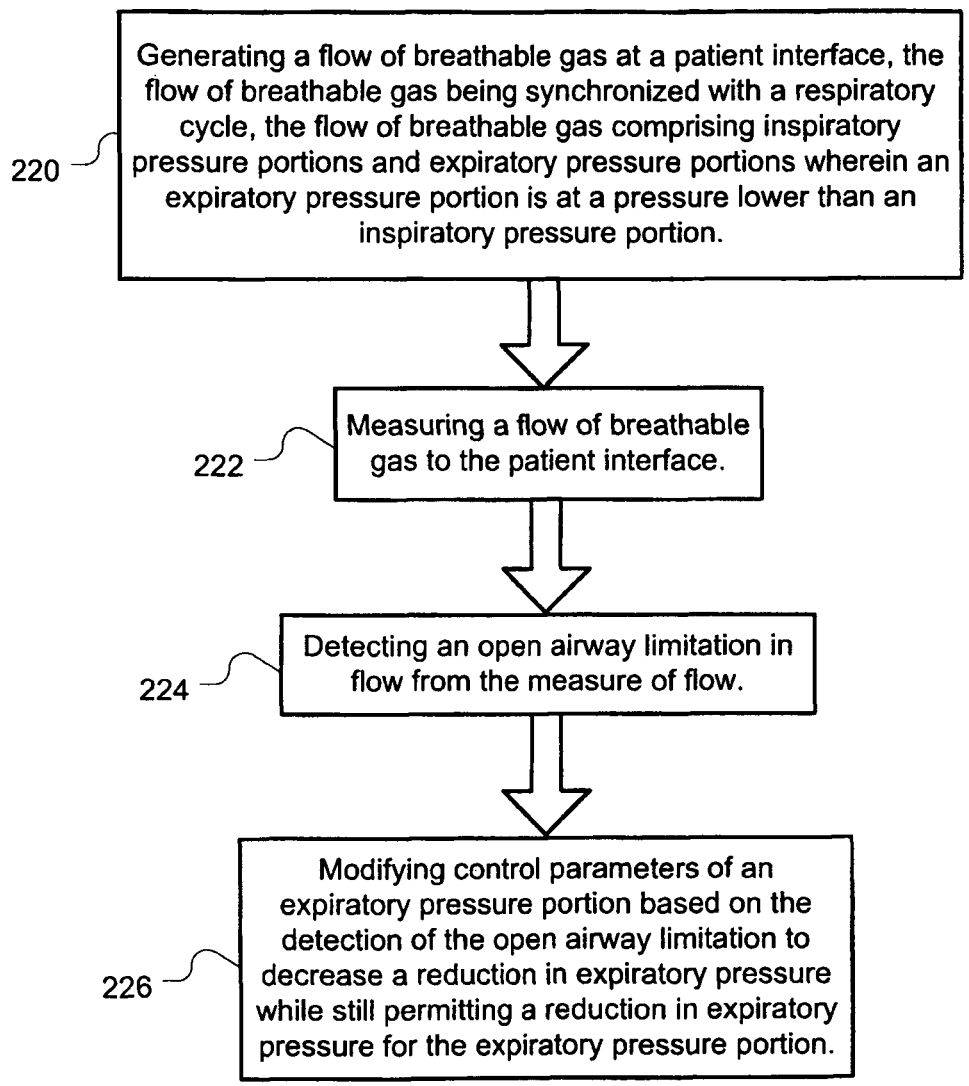
FIG. 2 is an example methodology for expiratory pressure relief control.

One such example methodology or algorithm of the controller 104 is illustrated in the flow chart of FIG. 2. At 220, the controller controls a respiratory pressure treatment apparatus 102 so as, to generate a flow of breathable gas at the patient interface. The flow of breathable gas can be synchronized with a respiratory cycle of the patient, for example, upon detection of inspiration or expiration through analysis of pressure and/or flow data from the sensors. The generated flow of breathable gas may then include inspiratory pressure portions and expiratory pressure portions so that the EPR level establishes an expiratory pressure portion at a pressure lower than an inspiratory pressure portion. At 222, the flow of breathable gas to the patient interface is measured, for example, with the flow sensor 106.

At 224, based on the measure of flow, the controller detects whether or not an open airway exists, which in some embodiments may be contemporaneous with a detection of and apnea and/or a reduction in a measure of patient airflow volume or patient ventilation. For example, the controller may determine whether or not a central apnea or a central hypopnea is occurring. In one such embodiment, the detection of central apnea may be made by any of the methodologies described in U.S. Pat. No. 5,704,345. For example, the detection of central apnea may be made by a determination of patency of the airway (e.g. an open airway) in conjunction with a significant reduction in patient respiratory flow below a threshold. The patency determination may be performed by applying an oscillatory pressure waveform of known frequency to a patient's airway, calculating the magnitude of the component of the flow signal at the known frequency induced by the oscillatory pressure waveform and comparing the calculated magnitude with a threshold value. Other methods for detection of central apnea may also be implemented.

In some embodiments, the central hypopnea may be determined by detecting both a hypopnea and an open airway. For example, the following may be detected: (a) a partial reduction in breathing or ventilation that lasts a period of time (e.g., at least 10 seconds) during sleep and (b) either an absence of partial obstruction or an open airway. For example, the controller may determine from the measure of flow a 10 second reduction in a measured volume of flow by at least 50%. It may also consider the absence of flow limitation (e.g., partial obstruction) by detecting an absence of flow flattening using a flattening index as discussed in U.S. Pat. No. 5,704,345. Patency may also be detected as described in U.S. Pat. No. 5,704,345. A flattening index may be a real number calculated using flow data from a patient's inspiratory waveform. An absence of partial obstruction may also be determined from a degree of roundness of the flow signal. Other methods for detection of hypopnea, open airway, partial reduction in breathing and partial obstruction may also be implemented. By way for further example, methods for determining hypopnea as disclosed in U.S. Patent Application No. 61/184,592, entitled "Methods and Devices for the Detection of Hypopnoea" filed on Jun. 5, 2009, the disclosure of which is incorporated herein by reference, may also be implemented. Similarly, methods of determining flow limitation or an absence thereof, may be implemented in accordance with PCT/AU2008/000647 (WO/2008/138040), filed on May 9, 2008, the disclosure of which is incorporated herein by reference.

At step 226, the controller may modify control parameters of an expiratory pressure portion based on the detection of an open airway, which may correspond with a contemporaneous detection of an apnea and/or a reduction in patient airflow, so as to decrease a reduction in expiratory pressure while still permitting a reduction in expiratory pressure for the expiratory pressure portion. For example, if an EPR level is currently set to level 3, upon detection of either a central apnea or a central hypopnea condition, the EPR level may be decremented to level 2. In response thereto, the flow generator would decrease the pressure reduction delivered during a subsequent expiratory phase. Because EPR is a reduction from the inspiratory level of treatment pressure (e.g., the CPAP treatment pressure), it will be recognized that these decreases in pressure reduction would result in a decrease in pressure support (PS).

In some embodiments, a continued detection of central apnea or central hypopnea condition (or additional detections) by the controller may further decrement the EPR level. If a sufficient number of central apneas are detected, the EPR level may be decremented to an EPR Level 0. In such a case, the pressure delivered by the flow generator under control of the controller would be essentially a relatively constant pressure across both inspiration and expiration. In some embodiments of this technology, this termination of the EPR reduction might be continued for the remainder of the treatment session (e.g., the nights sleep session.) such that the CPAP pressure will continue to be delivered during subsequent expiratory phases of the patient's respiratory cycles of the session. In such a case, the resetting of the EPR reductions can be enabled once the apparatus is reset or restarted for a new treatment session.

However, in some applications of the technology, the EPR Level may be incremented thereafter if the controller detects an absence of an open airway that corresponds with an apnea and/or a reduction in patient airflow volume for a period of time in a post-detection pause. For example, if after several minutes or after a predetermined number of respiratory cycles, central apneas and central hypopneas are no longer detected, the level of EPR may be incremented or reset to the maximum comfort level (e.g., EPR level 3). Optionally, incrementing of the EPR level may be gradual so as to eventually increase the EPR to a maximum level to provide a maximum EPR comfort pressure setting in the continued absence of the detection of the open airway apnea or patient airflow reduction. For example, additional increments to the EPR may be made if after several minutes or after a predetermined number of respiratory cycles, central apneas and central hypopneas are still not detected.

Figure 3:
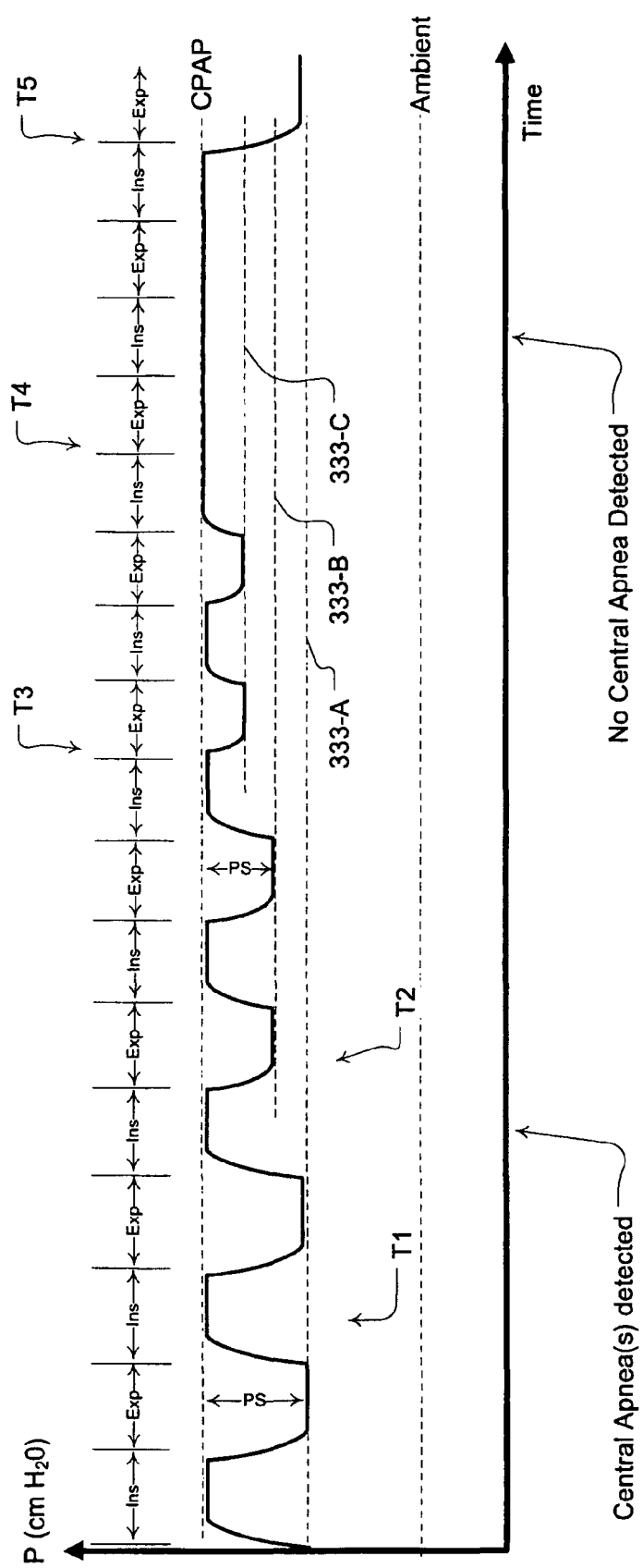
FIG. 3 illustrates an example pressure waveform with adjustments in accordance with the methodology of FIG. 2.

An example pressure treatment according to such control methodology is illustrated in FIG. 3. As shown at T1, the waveform initially illustrates a pressure treatment at an EPR Level 3 at line 333-A. As shown at T2, upon detection of a central apnea or central hypopnea, the EPR level is reduced to the EPR Level 2 shown at line 333-B. As shown at T3, upon continued detection of the central apnea or central hypopnea, the EPR level is again reduced to EPR Level 1 shown at line 333-C. As shown at T4, upon still continued detection of the central apnea or central hypopnea, the EPR level is again reduced to EPR Level 0 such that it remains at the same pressure as the CPAP pressure during both phases of the respiratory cycle (i.e., inspiration and expiration). As shown at T5, after a post-detection pause, a chosen level of EPR may then resume. Optionally, this resumption setting may be to the most comfortable setting (e.g., EPR Level 3) as shown or the level may gradually increment to the most comfortable setting with each increment occurring after a period of time (e.g., minutes or a chosen number of respiratory cycles) without a detection of the central events.

B. Persistent Obstruction EPR Adjustments

Figure 4:
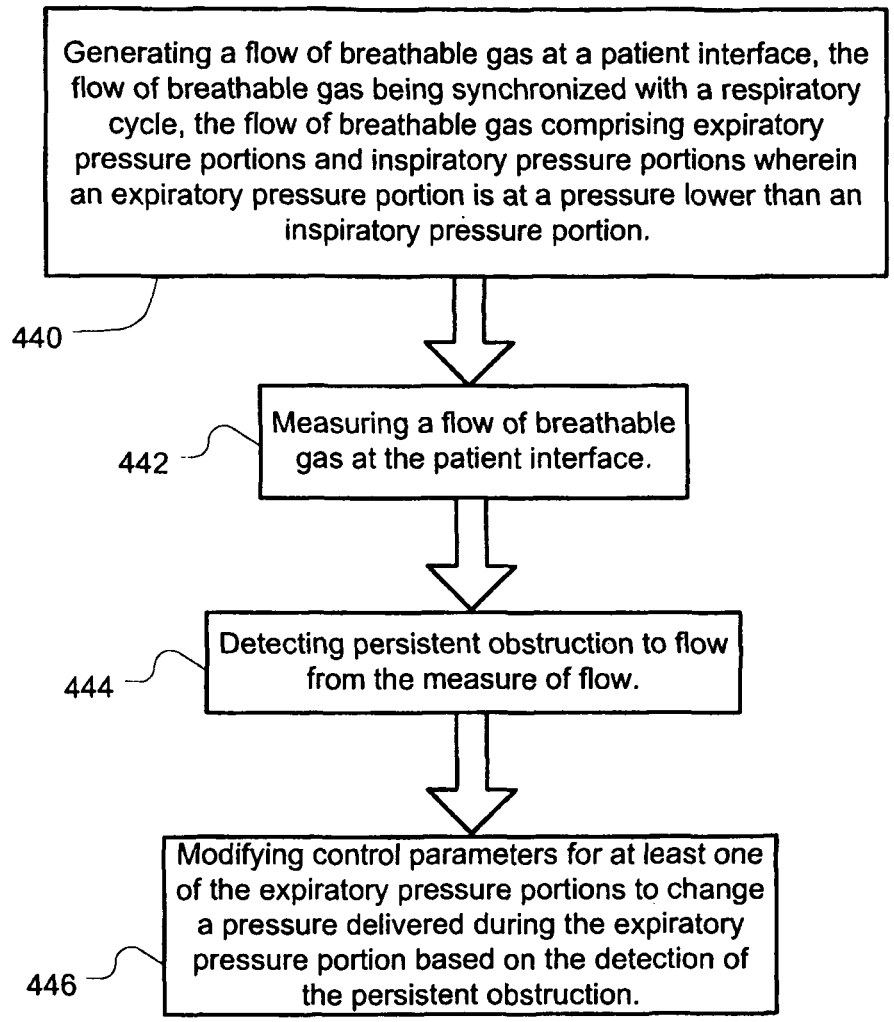
FIG. 4 is an further example methodology for expiratory pressure relief control.

In some versions of the present technology, the selection of the level of EPR may be automated based on the detection of one or more SDB events by the example methodology or algorithm of the controller 104 as illustrated in the flow chart of FIG. 4. At 440, the controller controls a respiratory pressure treatment apparatus 102 so as to generate a flow of breathable gas at the patient interface. The flow of breathable gas can be synchronized with a respiratory cycle of the patient, for example, upon detection of inspiration or expiration through analysis of pressure and/or flow data from the sensors. The generated flow of breathable gas may then include inspiratory pressure portions and expiratory pressure portions so that the EPR level establishes an expiratory pressure portion at a pressure lower than an inspiratory pressure portion. At 442, the flow of breathable gas to the patient interface is measured, for example, with the flow sensor 106.

At 444, based on the measure of flow, the controller detects whether or not a persistent obstruction to flow exists. For example, the detection of persistent obstruction may be determined from a measure of flow limitation, partial obstruction, obstructive apnea, flow flattening and or flow roundness that does not substantially change during a period of time such as a number of minutes (e.g., 5 or more) or a number of respiratory cycles (e.g., 10 or more). During such time, the controller may attempt to treat the detected obstruction with one or more successive increases to the CPAP treatment pressure that is delivered during inspiration, but the set EPR level would remain unchanged. Thus, the pressure support may stay the same during this treatment adjustment period. In some embodiments, the persistent obstruction may be determined based on the existence of detected obstruction despite repeated changes to a therapy pressure. (e.g., (a) several step increases in the CPAP pressure and the continued presence of partial obstruction or (b) several such increases up to a maximum CPAP pressure and the continued presence of partial obstruction).

At 446, the controller 104 would then automatically modify control parameters for at least one of the expiratory pressure portions to change a pressure delivered during the expiratory pressure portion based on the detection of the persistent obstruction. For example, in the event that one or more treatment changes does not resolve the obstruction and/or the detected airway obstruction continues to exist for the period of time, this detection of persistent obstruction can serve as logic to control a reduction of the EPR level, such as a decrement of the currently set EPR level. In the event that the persistent obstruction condition remains after a further period of time (e.g., minutes or cycles), then the EPR level may again be decremented. Additional decrements may also be implemented to eventually reduce the EPR level to the EPR Level 0 at which time there would be no reduction in pressure during expiration.

Figure 5:
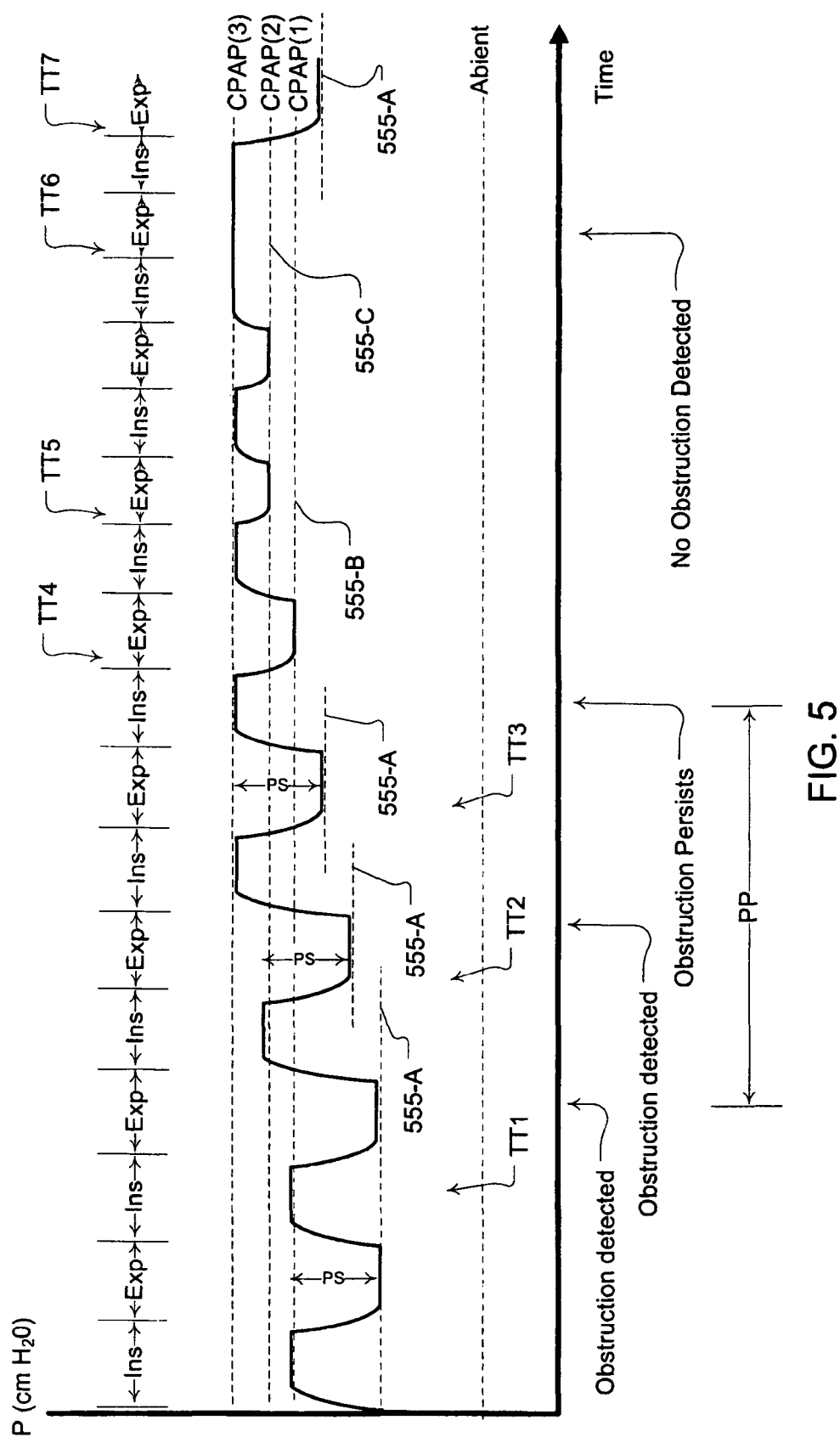
FIG. 5 illustrates an example pressure waveform with adjustments in accordance with the methodology of FIG. 4.

An example pressure treatment according to such a control methodology is illustrated in FIG. 5. As shown at TT1, the waveform initially illustrates a pressure treatment at an EPR Level 3 at line 555-A. As shown at TT2, upon detection of partial obstruction (e.g., flow flattening, degree of roundness or flow limitation, etc.), the CPAP treatment pressure or SDB therapy pressure may be increased. Since, the EPR level is unchanged at line 555-A, the pressure support (PS) remains the same with respect to the prior respiratory cycle at TT1.

At TT3, another obstruction is detected or the same obstruction is detected. Since the persistence period PP has not lapsed, which may be determined by a timer or respiratory cycle counter and a threshold, a CPAP pressure treatment increase is applied. Again the previously set EPR level and the pressure support PS remains the same.

However, at TT4, since the obstruction is still detected and a persistence time period PP has lapsed or the maximum CPAP pressure has been reached, the EPR level is decremented so that the expiratory pressure relief is reduced as shown at line 555-B. Consequently, the pressure support is also reduced. Again at TT5, since obstruction is still detected, the EPR level is decremented so that the expiratory pressure relief is reduced as shown at line 555-C with a consequent reduction in pressure support. Similarly at TT6, since obstruction is still detected, the EPR level is decremented so that the expiratory pressure relief is reduced to EPR level 0 so as to maintain the CPAP pressure of inspiration during expiration. Finally, at TT7, obstruction is no longer detected and an optional pause period as previously mentioned has lapsed. Thus, the EPR level may be incremented or reset to the most comfortable setting. However, in some embodiments of this technology, once the EPR reduction has been terminated upon reaching EPR Level 0, this termination might continue for the remainder of the treatment session (e.g., the nights sleep session.) or until the apparatus is reset or restarted for a new treatment session.

In the above pressure treatment illustrations, consecutive decreases in the EPR level may be controlled in consecutive respiratory cycles in the presence of a detection of obstruction in each such cycle. However, in some embodiments, each consecutive decrease may be made after an optional pause time period, (e.g., several respiratory cycles) to provide the device an opportunity to impact the detected obstruction at the new EPR level setting before an additional decrease in the EPR level is made. An example of such a change is illustrated between time markers TT5 and TT6.

Additionally, although the illustrated pressure waveforms of FIGS. 3 and 5 show that there is no increase to the EPR Level setting until reaching the lowest EPR level, such an increase may be made before the lowest EPR level (i.e., a level with no EPR pressure reduction) in the absence of a detection of obstruction or central hypopnea or central apnea. Thus, in FIG. 5, if at TT5 no obstruction had been detected and an optional pause time period has lapsed, the control of the device may make an increase in the EPR level to increase the reduction of expiratory pressure from the CPAP treatment pressure. Similarly, in FIG. 3, if at T3 no central events had been detected and an optional pause time period has lapsed, the control of the device may make an increase in the EPR level to increase the reduction of expiratory pressure from the CPAP treatment pressure.

Optionally, one or more of the aforementioned features may be combined with methods for automated adjustments to end expiratory pressure (auto-EEP). For example, an auto-EEP algorithm might also be implemented into the controller to make adjustments to the end expiratory pressure in an attempt to abolish closed-airway apnoeas. These adjustments may be attempted before making the aforementioned adjustments that would reduce the EPR level and thereby before making any reduction to the pressure support. Optionally, the EEP algorithm could also determine an EEP that is a minimum pressure required to abolish obstructive apnoeas. This could then be implemented so as to prevent an automated selection of an EPR level that would permit the pressure set during expiration to go below the established minimum EEP. For example, when incrementing to a higher EPR level, a check might first compare the possible resultant expiratory pressure (i.e., CPAP_pressure minus EPR_pressure) and only permit the EPR level change if the resultant pressure would be higher than the minimum EEP.

In still further modifications of the technology, pressure adjustments based on the detection of SDB events may be made to the EPR level before making modifications to the CPAP treatment pressure. For example, the logic of the controller may be configured to automatically decrease the EPR level when one or more SDB events are detected. This may be done incrementally. If the problem persists, such as if a time period has elapsed and the obstruction is still detected or if the EPR has been incrementally reduced to level 0 and SDB events are still detected, then automated adjustments may be made to the CPAP treatment pressure (e.g., with automated increments of the CPAP pressure up to a maximum CPAP treatment pressure). An example of a device with such an automated control of the CPAP treatment pressure level is described in U.S. Pat. No. 5,704,345. Optionally, such automated pressure adjustments may be made by shifting the pressure curve.

C. Obstructed Airway Inspiratory Adjustments

Figure 6:
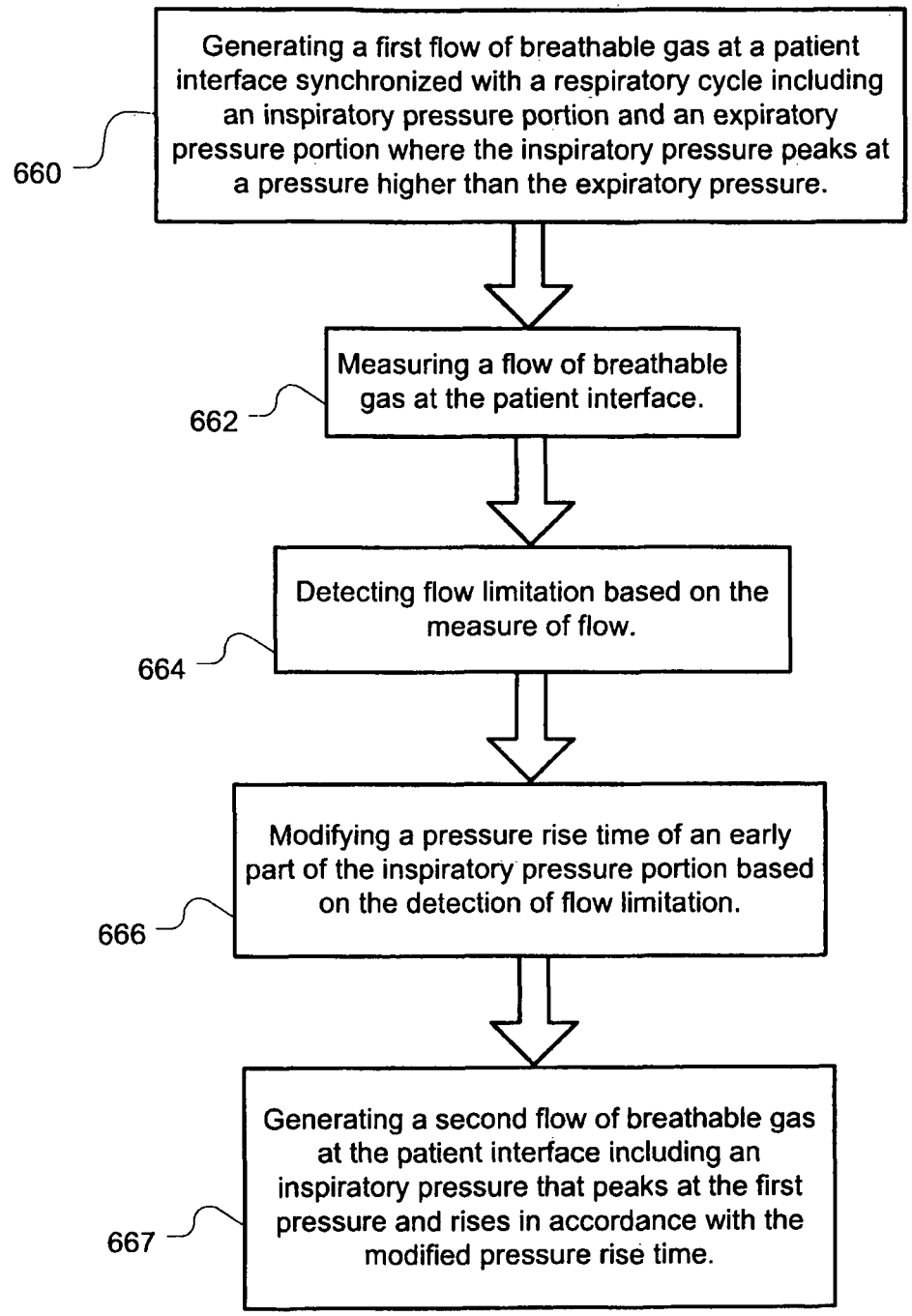
FIG. 6 is a further example methodology for pressure treatment control of the present technology.

In some embodiments of the present technology, the control settings for returning the pressure to the CPAP level during inspiration from the level of pressure reduced by the EPR setting may also be automatically adjusted based on the detection of one or more SDB events. An example of such an automated control methodology or algorithm of the controller 104 is illustrated in the flow chart of FIG. 6. At 660, the controller controls a respiratory pressure treatment apparatus 102 so as to generate a flow of breathable gas at the patient interface. The flow of breathable gas can be synchronized with a respiratory cycle of the patient, for example, upon detection of inspiration or expiration through analysis of pressure and/or flow data from the sensors. The generated flow of breathable gas may then include inspiratory pressure portions and expiratory pressure portions. With the EPR settings, the inspiratory portion can peak at a pressure that is higher than the pressure delivered during expiration. At 662, the flow of breathable gas to the patient interface is measured, for example, with the flow sensor 106. At 664, based on the measure of flow, a measure of partial obstruction or flow limitation is determined.

At 666, based on the detection of flow limitation, the controller can modify a pressure rise time of an early, part of the inspiratory pressure portion. The controller can then control a generation of a further flow of breathable gas at, the patient interface with an inspiratory pressure that peaks at the pressure from the prior inspiratory cycle but rises according to the pressure rise time modification.

Figure 7:
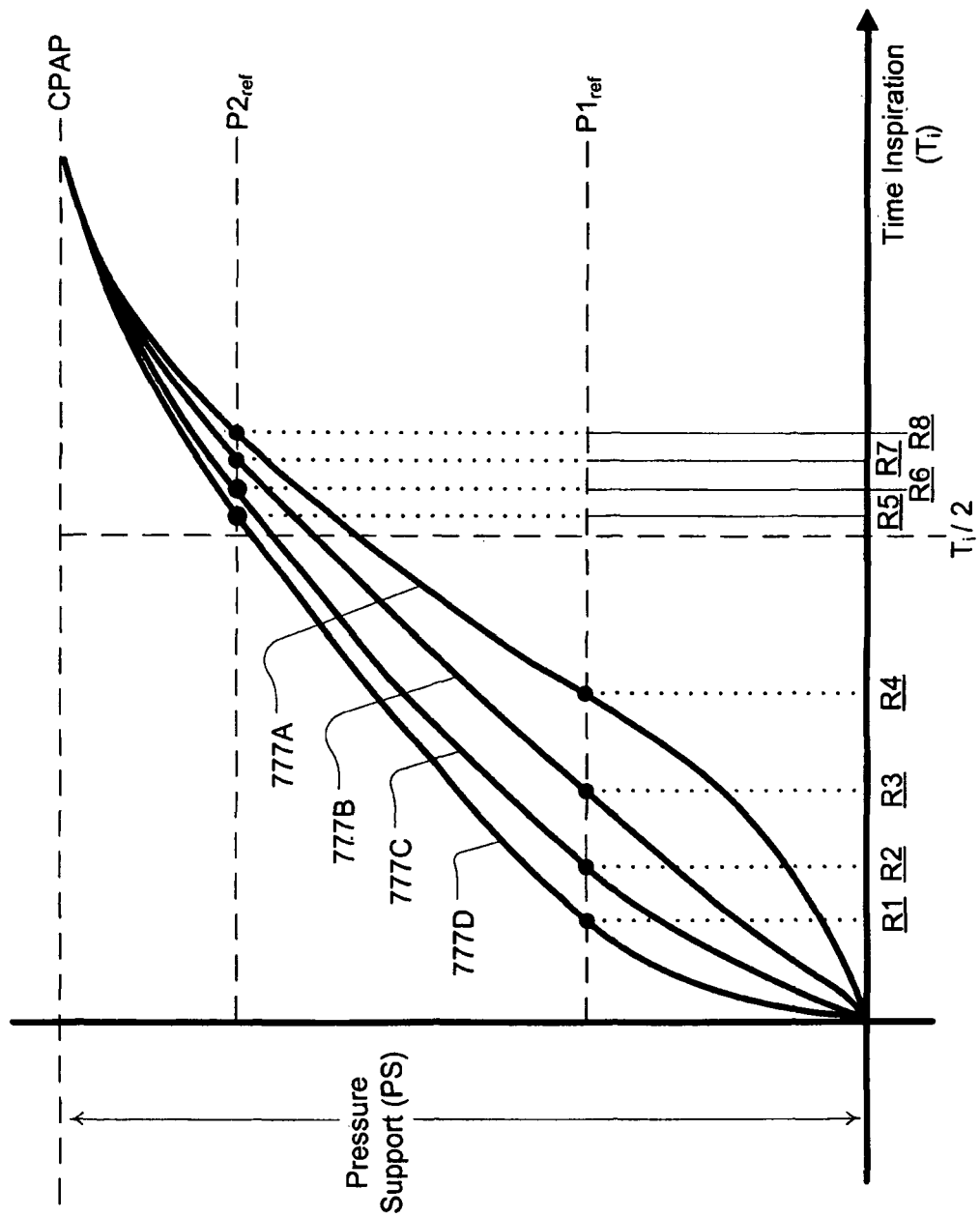
FIG. 7 illustrates several example inspiratory pressure waveforms with adjustments in accordance with the example methodology of FIG. 6.

Example inspiratory pressure waveforms that may be controlled by the aforementioned methodology are illustrated in the graph of FIG. 7. In this example, although the number of different waveforms can be changed, four inspiratory waveforms are shown that may be selectively generated by the controller as a function of a detection of partial obstruction or flow limitation. As illustrated, waveform 777A may be considered a least aggressive inspiratory waveform. When considered with a shared peak at the CPAP pressure level, the remaining waveforms 777B, 777C and 777D, have rise times R3, R2, and R1 in their early portions (e.g., before middle inspiration at $T_i/2$) with respect to a reference pressure level $P1_{ref}$ that are lesser than the rise time R4 of the early part of waveform 777A. When considering a peak at a common CPAP pressure level, the latter portions may also have different rise times. In the example, the rise in a latter portion of the waveform 777A has a shorter rise time (R8 minus R4) than the rise time (R7 minus R3) of the waveform 777B with respect to reference pressure levels $P1_{ref}$ and $P2_{ref}$. Similarly, waveform 777A has a shorter rise time (R8 minus R4) than the rise time (R6 minus R2) of the waveform 777C and shorter than the rise time (R5 minus R1) of waveform 777D.

As illustrated, the early portions of the waveforms may be characterized as being progressively more aggressive. In this regard, waveform 777B is more aggressive than 777A. Similarly, waveform 777C is more aggressive than 777B and waveform 777D is more aggressive than 777C. In embodiments of the present technology, the flow generator may progressively deliver more aggressive waveforms as a function of detected obstructive events.

For example, an obstruction or flow limitation index may be used for a scaling function or for an index to a look-up table for adjustment of the pressure verses time inspiratory flow curve. One example is illustrated in the table of FIG. 8 which can be implemented in a pressure delivery equation such as the following:

Pressure=[RESP*EPR*$F(O_j, T_i)$]+[CPAP−EPR];

where:
RESP is 1 for detected inspiration and 0 for detected expiration;
CPAP is a therapeutic pressure for treatment of sleep disordered breathing events;
EPR is the pressure of the currently set EPR level;
$O_j$ is an obstruction index such as a flow limitation index or a flow flattening index;

$T_i$ is a time index during inspiration;
F is a function to obtain a rise time scaling factor from the table illustrated in FIG. 8 based on an inspiratory time index (e.g., $T_1, T_2, T_3 \ldots T_N$) and the obstruction index. This data of the table may implement an adjustment of the pressure setting according to data representing the rise time profiles illustrated in FIG. 7. In this example, for higher obstruction indices where there is a greater degree of partial obstruction, the rise time of the early portion of the pressure waveform is lower to implement more aggressive waveforms. For lower obstruction indices where there is a lower degree of partial obstruction, the rise time of the early portion of the pressure waveform is higher to implement less aggressive inspiratory waveform. However, the peak pressure during inspiration may still rise to the CPAP treatment pressure. This CPAP treatment pressure setting may be determined and adjusted by other methods (e.g., by automatic detection or a manual setting). Upon detection of expiration, the pressure equation will regulate the pressure at the EPR level below the CPAP treatment pressure setting.

According, with such a system having expiratory pressure relief (EPR) and less aggressive inspiratory waveforms (e.g., a gentle rise time), an SDB patient may experience greater comfort while falling asleep or progressing from an awake state to sleep state. However, these comfort adjustments might not be necessary once the patient is in a sleep state (except in the case of high CPAP pressure treatment settings such as a pressure above ~14 cmH$_2$0 in which case it will more than likely improve comfort during sleep as well).

For example, a gentle rise time during sleep might permit a patient's airway to begin to experience partial obstruction and become unstable. If the pressure support (PS) is not aggressive enough, it may lead to airway collapse (obstructive apnea). Accordingly, when a patient begins to fall asleep, and the obstruction index is at 0, the delivered waveform would be least aggressive and most comfortable permitting the patient to fall asleep easier. However, as the patient's airway begins to obstruct and flow limitation is detected, the obstruction index will increase and thereby adapt the waveform to increase the aggressiveness of the early inspiratory part of the waveform according to the above methodology.

D. Sleep State Based Pressure Adjustments

In some embodiments of the technology, pressure adjustments, such as the level of EPR and/or aggressiveness of early inspiratory pressure, may be automated based on a detection of a sleep state of a patient using the respiratory pressure treatment apparatus 102. In such embodiments, the controller may be implemented as or with a sleep state detector. For example, the controller may use signals or data from one or more of electroencephalogram (EEG), Electrocardiography (ECG), blood gas saturation (e.g., Pulse-Oximeter), Effort Bands, Accelerometer, Non-contact respiratory flow/ECG sensor, respiratory flow sensor and/or any other sensor means to determine or calculate sleep states of a patient. Thus, the controller may be configured to differentiate between Awake, REM Sleep and NREM Sleep states based on the signals or data. An example of a suitable sleep state detector is described in International Patent Application No. PCT/AU2010/000894, the disclosure of which is incorporated herein by reference. Such a controller may then have EPR settings and/or rise time settings that are associated with different detectable sleep states in a memory of the apparatus.

With such a controller, EPR may be primarily used as a comfort feature, helping the patient expire against a lower pressure during wakefulness/sleep onset, where breathing still has some level of voluntary control. It may not be necessary then for the controller to implement EPR during REM and NREM sleep states. Thus, in some embodiments of the technology the EPR may be activated or deactivated depending on sleep state, such as being activated when an AWAKE state is detected and/or deactivated when a REM or NREM state is detected.

In some embodiments, the controller of the treatment apparatus may be configured to set EPR and/or aggressiveness of inspiratory pressure rise time with one or more of the following treatment options based on sleep state:

i.) During a detected AWAKE State the EPR may be set by the controller to a high level (e.g., EPR level 3). Once the controller detects that the patient's sleep state has changed to a SLEEP state (either REM or NREM states), the controller may adjust down the EPR level from an awake level (e.g., a high or higher EPR) to a sleep level (e.g., a low or lower level or a zero level EPR). Optionally, this adjustment may be ramped down such as by successively decrementing the previously set EPR level over a pre-set time period (e.g., 1 level per consecutive 5 minute interval) or a pre-set number of respiratory cycles (e.g., 1 level per 10 detected respiratory cycles) until the EPR reaches the desired sleep level, which may be a preset in the settings of the controller.

In such embodiments, the EPR level during sleep can be decremented to any suitable or preset EPR level depending on what is appropriate for the patient (e.g., from Level 3 to level 0 or level 3 to level 1). Thereafter, if the patient is sleeping and the controller detects a transition into an AWAKE state, then the controller may be configured to raise the EPR level, such as by ramping up, to a suitable awake level from the presently set sleep level. Optionally, the ramp period (either up or down) may be set to any value by input from a physician to adjust configuration parameters of the controller, depending on what is appropriate for the patient. Thus, the controller may successively increment (or decrement) the EPR level over a pre-set time period (e.g., 1 level per consecutive 5 minute interval) or a pre-set number of respiratory cycles (e.g., 1 level per 10 detected respiratory cycles) until the EPR level, is set to the desired awake (or sleep) level.

ii.) During a detected AWAKE state, the controller may adjust or set the EPR level and may also adjust and/or set a rise time at suitable levels as previously discussed. Once the controller detects that the patient's sleep condition has changed to a SLEEP state (e.g., either a REM state or NREM state), the rise time setting of the early portion of the inspiratory waveform may be reduced by the controller to a sleep level (e.g., to be more aggressive in the nature of its response). Optionally, this reduction may be an incremental change so as to make the change gradual over a chosen time period or number of respiratory cycles, etc. In this way, a suitable rise time may be pre-set in the apparatus to have an association with a sleep state. This pre-set rise time may be manually input by a physician or anyone else who is administering therapy for the patient.

Optionally, the detection of a sleep state indicative of sleep may initiate the previously discussed automated control algorithm that adjusts the rise time (inspiratory portion aggressiveness) based on the automated detection of the SDB events (e.g., flow flattening or obstruction) so as to deliver progressively more aggressive rise times with the detection of such events and less aggressive rise times in the absence of the detection of such events. If the patient is sleeping and transitions into an AWAKE state, the rise time may be changed (e.g., by ramping incrementally) to an awake level (thereby making the nature of the response less aggressive). This Awake state may then also serve as a basis to control disengaging of the control protocol that changes the rise times in response to the detection of SDB events.

E. Pressure Adjustments by Ventilation

In some embodiments, the controller may be configured to determine a measure of ventilation. Such a measure may be, for example, a volume derived from a flow signal such as a tidal volume, a minute volume or a low pass filtered absolute value of a flow signal divided in half. Other measures of ventilation may also be implemented. Such measures of ventilation may in turn serve as part of the logic of the controller for selecting or setting the EPR level and/or rise time profile. In this respect, the EPR level or rise time profile may be set in response to the ventilation parameter as opposed to an obstructive breathing detection index such as apnea index, flow flattening, snore, etc.) For example, the ventilation measure, such as certain detected decreases, may control a decrease in the EPR level and/or a more aggressive inspiratory rise time profile (e.g., a profile with a shorter rise time). Moreover, detected increases in the ventilation measure may also serve to control or permit increases in the EPR level and/or a less aggressive inspiratory rise time profile (e.g., a profile with a longer rise time). In one such embodiment, if the ventilation falls below a target ventilation (such as a pre-set ventilation target or an average ventilation determined from a prior treatment session or a prior period of treatment) by some threshold amount, the drop may trigger the controller to make a decrease in the EPR level and/or an increase in the aggressiveness of the rise time of the early inspiratory portion of the pressure wave form. Additional ventilation drops may trigger yet further EPR level reductions and/or rise time decreases down to some minimum. Similarly, in one such embodiment, if the ventilation rises above a target ventilation by some threshold amount, the rise may trigger the controller to make an increase in the EPR level and/or an decrease in the aggressiveness of the rise time of the early inspiratory portion of the pressure wave form. Additional ventilation rises may trigger yet further EPR level increases and/or rise time increases up to some maximum.

F. Certain Recurring Events

In some embodiments, upon detection of several recurring SDB events, over-ventilation and/or long pauses that are not long enough to be a central apnea, an automated adjustment to pressure may involve an increase of the pressure support baseline and reduction of the pressure support or a reduction of CPAP and pressure support.

G. Pre-Termination Treatment Adjustments

In some embodiments, the controller may be configured to make adjustments to the treatment protocol in conjunction with an anticipated or detected ending of a treatment session. This may permit patients to wake more comfortably by initiating pressure changes to more comfortable levels (e.g., lower) from more therapeutic levels (e.g., higher) at or near the time that the patient wakes up from sleep. Such a treatment adjustment may be particularly helpful where higher therapy levels are utilized during sleep, such as in the case of Chronic Obstructive Pulmonary Disease (C.O.P.D.) patients.

For example, the controller may be configured with a timer or clock and a time threshold may be determined or set (e.g., by the patient) to a particular time at which the patient using the device will wake up from sleep and/or the apparatus will be turned off (automatically or manually). Thus, the set time can serve as a timing threshold that may be compared with a timer or clock of the apparatus. This set time may then represent a wake up time or the time the patient will stop a current treatment session with the respiratory treatment apparatus. With such an ending time, the controller may be configured with a pre-termination control methodology that modifies the treatment settings of the device for the patient during a period of time (e.g., a number of minutes etc.) that immediately precedes the termination time when the patient will wake up or the apparatus will be turned off. For example, this pre-termination period may be initiated when a timer of the apparatus exceeds the timing threshold less the amount of time of the pre-termination period. A pre-termination treatment protocol may be initiated by the controller during this time period.

For example, in some embodiments, during this pre-termination period, the EPR may be initiated (e.g., activated) or the EPR level may be gradually increased.

Figure 10:
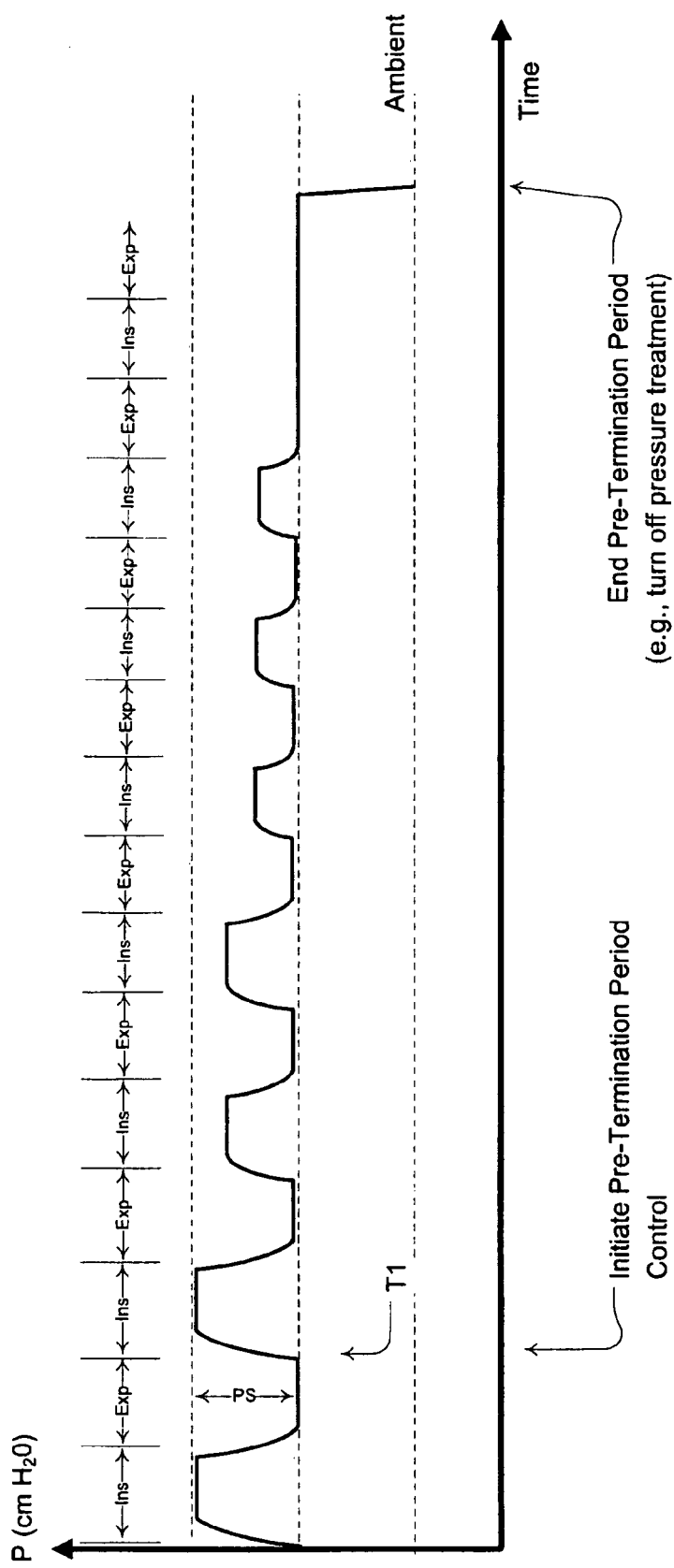
FIG. 10 is a graph of a pressure time curve illustrating a ramp down procedure.

In some embodiments, during this pre-termination period, the therapeutic treatment pressure setting (e.g., the peak pressure level associated with an IPAP) may be reduced or gradually ramped down by the controller of the apparatus. Optionally, this reduction or gradual ramp down may be to the level of pressure of the EPR setting at the time that the apparatus initiates the pre-termination period. For example, if the therapeutic treatment pressure is at 10 cm $H_2O$ and the EPR is set at level 3 at the time that the pre-termination period is initiated by the controller, the therapeutic treatment pressure may be gradually ramped down to the effective pressure level of the EPR setting. (e.g., 10 cm $H_2O$ minus 3 cm $H_2O$=7 cm $H_2O$) over the course of the pre-termination period such that the pre-termination period starts at a higher pressure and ends at a lower pressure. For example, this typically will take place over a number of respiratory cycles or a time on the order of minutes, as opposed to in a single respiratory cycle. Optionally, the pressure time curve of the ramping down of pressure over this pre-termination period may be linear or it may be some other function such as a step-wise function or other curve. Still further, the treatment pressure may be ramped down to some other pre-set pressure level from the level at which the treatment pressure setting was set at the time of initiation of the pre-termination period. An example ramp down during a pre-termination period is illustrated in the pressure verses time graph of FIG. 10. Although FIG. 10 illustrates a ramping down of treatment pressure, in some embodiments the control change during the pre-termination period may include either additionally or alternatively a change of the rise time profile of the inspiratory pressure. This rise time profile change may involve controlling a gradual change from more aggressive to less aggressive pressure time profiles over the course of the pre-termination time period.

Optionally, in some embodiments, the controller may be configured with logic to estimate a time when the patient will wake or terminate treatment with the apparatus so as to assess a suitable time to initiate the pre-termination period. For example, it may judge that a patient is likely to wake up at a certain amount of time after beginning treatment (e.g., some machine run time or machine use time in a range of 6 to 8 hours from the start of treatment). This estimate may serve as the timing threshold. Optionally, the timing threshold may be determined by the controller monitoring the machine run time or the time of use by the patient in one or more prior treatment sessions. For example, an average run time or average time of use of several prior treatment sessions may be determined and used to predict when a new treatment session is likely to end so as to serve as the timing threshold.

Still further, in some embodiments the triggering of the pre-termination period with the timing threshold may be based on sleep state detection as well. For example, the time for termination of treatment may not be based just on device use. Rather, it may be based on an amount of time in a treatment session that the patient treated with the device while the device detected a sleep state. For example, the timing threshold might be set to an amount of time that the patient was being treated while in a detected REM state. This REM state based timing threshold may be pre-set or it may be a calculated REM state time, or portion thereof, from one or more prior treatment sessions. In such a case it may be an average REM state time from prior sessions. Thus, the pre-termination period may be triggered as a function of a detected lapsed REM sleep time in a current treatment session.

Still further, the termination period may be initiated based on a detection of wake related events, which may be in conjunction with a timing threshold. For example, EEG signals or effort band signals may be processed by the controller to detect that the patient is waking up. If the signals contain an indication that the patient is waking up and/or a timing threshold has been reached such as one of the threshold previously discussed, the apparatus may initiate the pre-termination period.

Still further the pre-termination period may be initiated by a patient manually. For example, a patient may simply press a button or other user control on the device to more immediately activate initiation of the pre-termination period. Thus, when a patient initially wakes up he or she may manually initiate the pre-termination period.

Example Architecture

Figure 9:
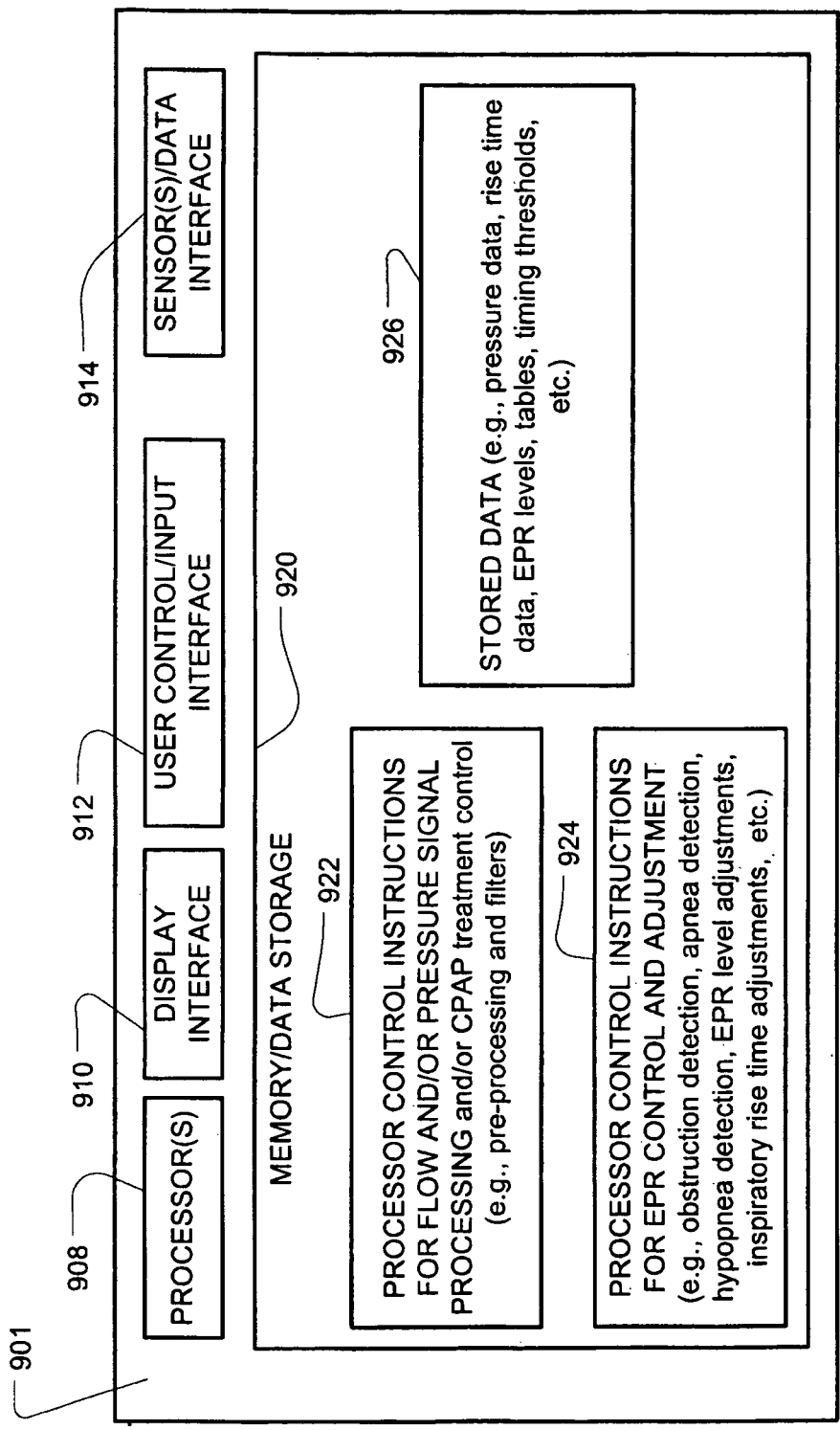
FIG. 9 illustrates a block diagram of an example controller architecture of the present technology.

An example system architecture of a controller suitable for the present technology is illustrated in the block diagram of FIG. 9. In the illustration, the controller 901 for the respiratory pressure treatment apparatus 102 may include one or more processors 908. The device may also include a display interface 910 to output SDB event detection reports (e.g., obstruction information and/or measures), results or graphs (e.g., pressure vs. time curves as illustrated in FIGS. 3, 5 and 7 or flow vs. time curves, etc.) as described herein such as on a monitor or LCD panel. A user control/input interface 912, for example, for a keyboard, touch panel, control buttons, mouse etc. may also be provided to activate or modify the control parameters for the methodologies described herein. The device may also include a sensor or data interface 914, such as a bus, for receiving/transmitting data such as programming instructions, rise time or pressure data, EPR level data, SDB event detection data etc. The device may also typically include memory/data storage components containing control instructions of the aforementioned methodologies (e.g., FIGS. 2-6). These may include processor control instructions for flow and/or signal processing and/or CPAP treatment control (e.g., pre-processing methods, filters, automated treatment pressure adjustment methodology) at 922 as discussed in more detail herein. They may also include processor control instructions for EPR Control and Adjustment (e.g., obstruction detection, apnea detection, hypopnea detection, EPR level adjustments, inspiratory rise time adjustments, etc.) at 924. Finally, they may also include stored data 928 for these methodologies such as pressure data, rise time data, timing thresholds, scaling factors, scaling functions, EPR levels, tables, timing thresholds, etc.)

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

A device in accordance with the present technology is suitable for use in the home of a patient, for example on a bedside table. Such devices often have a volume of approximately 2 to 3L and are quiet enough for a patient to sleep in close proximity. A device suitable for incorporating the present technology is the ResMed S9 CPAP device. Commonly such devices are available only on prescription. Depending on the healthcare system in a particular country, patients may be entitled to a reimbursement of some or all of the cost of the device from a government agency, or a healthcare insurer. Devices in accordance with the present technology may be used with a humidifier, e.g. ResMed H5i, to improve patient comfort.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" have been used herein, unless otherwise specified, the language is not intended to provide any specified order but merely to assist in explaining distinct elements of the technology. Furthermore, although process steps in the detection methodologies have been illustrated in the figures in an order, such an ordering is not required. Those skilled in the art will recognize that such ordering may be modified and/or aspects thereof may be conducted in parallel. Moreover, although the features described herein may be utilized independently, various combinations thereof may be made in a respiratory pressure treatment apparatus. Other variations can be made without departing with the spirit and scope of the technology. For example, a controller may be configured with the control logic to make different combinations of the automated adjustments of the CPAP treatment pressure, the EPR level and/or the aggressiveness of the inspiratory portion of the pressure waveform based on the detection of SDB events or obstruction detection. For example, an automated detection of an obstructive event may be initially treated by increasing the aggressiveness of the inspiratory portion of the waveform (e.g., by one increment or incrementally to its maximum aggressiveness). If the event persists (e.g., over a time period or lapsing of one or more respiratory cycles), the controller may then decrease the EPR level (e.g., by one decrement or incrementally to its lowest level). If the event still persists (e.g., over a further time period or lapsing of one or more additional respiratory cycles), the controller may then increase the CPAP treatment pressure level. (e.g., by one increment or incrementally to its maximum pressure setting). Still further embodiments may be made with different orders and combinations of these adjustments.

The invention claimed is:

1. A method of control for a respiratory pressure treatment apparatus comprising:
generating a flow of breathable gas at a patient interface with a respiratory pressure treatment apparatus, the flow of breathable gas being synchronized with a respiratory cycle, the flow of breathable gas comprising expiratory pressure portions and inspiratory pressure portions wherein an expiratory pressure portion is at a pressure lower than an inspiratory pressure portion by a level of expiratory pressure relief;
measuring a flow of breathable gas at the patient interface;
detecting obstruction to flow from the measure of flow with a controller of the respiratory treatment apparatus and successively increasing pressure of the inspiratory pressure portions in response to obstruction detections while maintaining a set level of expiratory pressure relief for the expiratory pressure portions;
detecting persistent obstruction to flow from the measure of flow with the controller of the respiratory treatment apparatus based on the successively increasing pressure of the inspiratory pressure portions; and
with the controller, modifying control parameters for at least one of the expiratory pressure portions to modify the level of expiratory pressure relief delivered during the expiratory pressure portion in response to the detection of the persistent obstruction, the modifying being a decrease in the level of expiratory pressure relief.

2. A respiratory pressure treatment apparatus comprising:
a flow generator to generate a flow of breathable gas to a patient interface;
a sensor to measure the flow of breathable gas; and
a controller to control the flow generator to deliver the flow of breathable gas at the patient interface, the flow of breathable gas being synchronized with a respiratory cycle, the flow of breathable gas comprising expiratory pressure portions and inspiratory pressure portions wherein at least one of the expiratory pressure portions is at a pressure lower than at least one of the inspiratory pressure portions by a level of expiratory pressure relief;
the controller to detect obstruction to flow from the measure of flow and to successively increase pressure of the inspiratory pressure portions in response to obstruction detections while maintaining a set level of expiratory pressure relief for the expiratory pressure portions;
the controller to detect persistent obstruction to flow from the measure of flow with the controller of the respiratory treatment apparatus based on the successively increasing pressure of the inspiratory pressure portions; and
the controller to modify control parameters for at least one of the expiratory pressure portions to modify the level of expiratory pressure relief delivered during the expiratory pressure portion in response to the detection of the persistent obstruction, the modifying being a decrease in the level of expiratory pressure relief.

3. The method of claim 1 wherein detecting obstruction to flow comprises a detection of partial obstruction or obstructive apnea.

4. The method of claim 1 wherein the modifying of the control parameters for the at least one expiratory pressure portion comprises disabling expiratory pressure relief during an expiratory phase.

5. The method of claim 1 further comprising discontinuing the modification of the control parameters of the expiratory pressure portion in response to a detection of an absence of persistent obstruction over a period of time.

6. The apparatus of claim 2 wherein the controller is configured to detect flow limitation by a detection of partial obstruction or obstructive apnea.

7. The apparatus of claim 2 wherein the controller is configured to modify the control parameters of the expiratory pressure portion as a disabling of expiratory pressure relief during an expiratory phase.

8. The apparatus of claim 2 further comprising discontinuing the modification of the control parameters of the expiratory pressure portion in response to a detection of an absence of persistent obstruction over a period of time.

9. The method of claim 1 wherein the controller determines occurrence of persistent obstruction to flow from a measure of obstruction that does not substantially change during a period of time.

10. The method of claim 9 wherein the period of time comprises a number of minutes.

11. The method of claim 9 wherein the period of time comprises a number of respiratory cycles.

12. The method of claim 1 wherein the controller determines occurrence of persistent obstruction to flow from an existence of detected obstruction despite repeated changes to a therapy pressure.

13. The method of claim 12 wherein the repeated changes to a therapy pressure comprises successive increases in treatment pressure delivered during inspiration.

14. The method of claim 13 wherein the repeated changes to a therapy pressure comprises increases in treatment pressure to a maximum pressure.

15. The apparatus of claim 2 wherein the controller is configured to determine occurrence of persistent obstruction to flow from a measure of obstruction that does not substantially change during a period of time.

16. The apparatus of claim 15 wherein the period of time comprises a plurality of minutes.

17. The apparatus of claim 15 wherein the period of time comprises a plurality of respiratory cycles.

18. The apparatus of claim 2 wherein the controller is configured to determine occurrence of persistent obstruction to flow from an existence of detected obstruction despite repeated changes to a therapy pressure.

19. The apparatus of claim 18 wherein the repeated changes to a therapy pressure comprises successive increases in treatment pressure delivered during inspiration.

20. The apparatus of claim 19 wherein the repeated changes to a therapy pressure comprises increases in treatment pressure to a maximum pressure.

21. The apparatus of claim 2 wherein the modifying of the control parameters comprises disabling expiratory pressure relief for a remainder of a treatment session.

22. The apparatus of claim 2 wherein the modifying of the control parameters comprises disabling expiratory pressure relief for a remainder of a treatment session until the apparatus is restarted for a new treatment session, the disabling of the expiratory pressure relief causing the apparatus to maintain a CPAP pressure of inspiration during expiration for the remainder of the treatment session.

23. The method of claim 1 wherein the modifying of the control parameters comprises disabling expiratory pressure relief for a remainder of a treatment session.

24. The method of claim 1 wherein the modifying of the control parameters comprises disabling expiratory pressure relief for a remainder of a treatment session until the apparatus is restarted for a new treatment session, the disabling of the expiratory pressure relief causing the apparatus to maintain a CPAP pressure of inspiration during expiration for the remainder of the treatment session.

* * * * *